US011999680B2

(12) United States Patent
Dunn et al.

(10) Patent No.: US 11,999,680 B2
(45) Date of Patent: *Jun. 4, 2024

(54) ENHANCED CONVERSION OF TAURINE TO ALKYL TAURATE AMIDE USING PHOSPHORIC ACID CATALYSTS

(71) Applicant: Conopco, Inc., Trumbull, CT (US)

(72) Inventors: Erin Whitfield Dunn, San Francisco, CA (US); Bijan Harichian, Irvine, CA (US); Anat Shiloach, Trumbull, CT (US); John Robert Winters, Dumont, NJ (US)

(73) Assignee: CONOPCO, INC., Englewood Cliffs, NJ (US)

( * ) Notice: Subject to any disclaimer, the term of this patent is extended or adjusted under 35 U.S.C. 154(b) by 903 days.

This patent is subject to a terminal disclaimer.

(21) Appl. No.: 17/047,089

(22) PCT Filed: Apr. 5, 2019

(86) PCT No.: PCT/EP2019/058706
§ 371 (c)(1),
(2) Date: Oct. 13, 2020

(87) PCT Pub. No.: WO2019/206607
PCT Pub. Date: Oct. 31, 2019

(65) Prior Publication Data
US 2021/0163405 A1    Jun. 3, 2021

(30) Foreign Application Priority Data
Apr. 24, 2018  (EP) ..................................... 18169068

(51) Int. Cl.
*C07C 303/22* (2006.01)
*B01J 27/16* (2006.01)
*C07C 309/15* (2006.01)

(52) U.S. Cl.
CPC ............ *C07C 303/22* (2013.01); *B01J 27/16* (2013.01); *C07C 309/15* (2013.01); *C07C 2527/173* (2013.01)

(58) Field of Classification Search
None
See application file for complete search history.

(56) References Cited

U.S. PATENT DOCUMENTS

| 2,880,219 A | 3/1959 | Burnette et al. |
| 3,150,156 A | 9/1964 | Lamberti |
| 3,232,968 A | 2/1966 | Schenck et al. |
| 5,384,421 A | 1/1995 | Day et al. |
| 5,434,276 A | 7/1995 | Walele et al. |
| 5,496,959 A | 3/1996 | Day |
| 11,059,776 B2 * | 7/2021 | Harichian ............. C07C 309/14 |

FOREIGN PATENT DOCUMENTS

| CN | 1680305 | 10/2005 | |
| CN | 1323069 | 6/2007 | |
| CN | 105175291 | 12/2015 | |
| CN | 106588709 | 4/2017 | |
| CN | 106588710 | 4/2017 | |
| JP | S327320 | 9/1957 | |
| JP | 57139056 | 8/1982 | |
| JP | 61129160 | 6/1986 | |
| JP | 2002234868 | 8/2002 | |
| JP | 2005008603 | 1/2005 | |
| WO | WO2018059889 | 4/2018 | |
| WO | WO-2019068494 A1 * | 4/2019 | ........... C07C 303/22 |

OTHER PUBLICATIONS

Lillian Becker; Safety Assessment of Alkyl Taurate Amides and Taurate Salts as Used in Cosmetics; Cosmetic Ingredient Review; Nov. 20, 2015; pp. 1-48.
Search Report and Written Opinion in EP17194640; Mar. 2, 2018; European Patent Office (EPO).
Search Report and Written Opinion in EP18169068; Oct. 12, 2018; European Patent Office (EPO).
Search Report and Written Opinion in PCTEP2018075747; Dec. 21, 2018; World Intellectual Property Org. (WIPO).
Search Report and Written Opinion in PCTEP2019058706; Jul. 10, 2019; World Intellectual Property Org. (WIPO).
Written Opinion 2 for PCTEP2018075747; Aug. 28, 2019; World Intellectual Property Org. (WIPO).
IPRP2 in PCTEP2018075747; Jan. 7, 2020; World Intellectual Property Org. (WIPO).
Burnette et al.; The Journal of the American Oil Chemists' Society; Reaction of Fatty Acids with N-Methyl Taurine; Mar. 23, 1962; pp. 477-478; vol. 39.
Co-pending Application, Harichian et al., U.S. Appl. No. 16/649,784, Mar. 23, 2020.
Park et al.; Development of Environmental-friendly N-Acyl Taurates Manufacturing Process and Evaluation of their Physical Properties; Clean Technology; Dec. 2005; pp. 195-204 with English translation; vol. 11, Issue 4.

* cited by examiner

Primary Examiner — Amy C Bonaparte
(74) Attorney, Agent, or Firm — Krista J. Aiello

(57) ABSTRACT

The invention relates to method of enhancing yield of alkyl taurate amides using enhancing specifically phosphoric acid catalysts. It further relates to the use of phosphoric acid to enhance yield while avoiding and/or reducing undesirable browning.

7 Claims, No Drawings

ENHANCED CONVERSION OF TAURINE TO ALKYL TAURATE AMIDE USING PHOSPHORIC ACID CATALYSTS

CROSS REFERENCE TO RELATED APPLICATIONS

The present application is a U.S. National Phase Application under 35 U.S.C. § 371 of International Application No. PCT/EP2019/058706, filed on Apr. 5, 2019, which claims priority to European Patent Application No. 18169068.6, filed on Apr. 24, 2018, the contents of which are incorporated by reference herein in their entireties.

FIELD OF THE INVENTION

The present invention relates to a method or process for enhancing yield of alkyl taurate amides ("ATA"), which are typically made from an amidation reaction of taurine or salts of taurine with fatty acid (e.g., $C_8$ to $C_{24}$ chain length fatty acid), using phosphoric acid catalysts.

BACKGROUND OF THE INVENTION

References disclosing production of alkyl taurate amides from the reaction of taurine and fatty acids are known.

U.S. Pat. No. 2,880,219 to Burnette, for example, teaches production of N-acyl taurates from fatty acids and taurines. From the table at column 7, it can be seen generally that conversion rates are pretty good although temperatures are all relatively high. There appears to be no catalyst used, let alone a discussion of how any particular catalyst might be unexpectedly superior than another.

"Reaction of Fatty Acids with N-Methyl Taurine" to Burnette and Chiddix discloses a similar reaction. There does not appear to be a disclosure of use of any catalyst at all.

U.S. Pat. No. 3,232,968 to Schenk discloses a process for preparing N-acyl taurates using specifically hypophosphoric acid. The superiority of phosphoric acid relative to other catalysts is not recognized.

Unexpectedly, applicants have found that, under otherwise identical process steps and conditions, use of phosphoric acid specifically (e.g., relative to other catalyst) is far superior.

SUMMARY OF THE INVENTION

The invention relates to a process of enhancing conversion of taurine to alkyl taurate amide. It has been found that use of specific catalyst, phosphoric acid catalyst, unexpectedly provides enhanced efficacy, all other parameters being identical.

More specifically the invention provides a process for making alkyl taurate amide, which process comprises reacting $C_8$ to $C_{20}$ fatty acid with taurine or taurine salt,
  wherein the molar ratio of fatty acid to taurine (or salt) is 1.5:1 to 10:1, preferably 1.6:1 to 7:1 or 1.9 to 5:1;
  wherein reaction temperature ranges from 180° C. to 250° C., preferably 190 to 245° C.;
  wherein the catalyst is phosphoric acid and is used in an amount of 0.1 to 0.7; preferably 0.1 to 0.5% by wt.; and
  wherein reaction time ranges from 1 to 10 hours, preferably 1 to 6 hours.

Use of specific phosphoric acid catalyst permits for more efficacy, i.e., greater yield is obtained, while simultaneously avoiding non-desirable browning.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about."

As used throughout, ranges are used as shorthand for describing each and every value that is within the range. Any value within the range can be selected as terminus of the range. The use of and/or indicates that any one from the list can be chosen individually, or any combination from the list can be chosen.

For the avoidance of doubt, the word "comprising" is intended to mean "including" but not necessarily "consisting of" or "composed of." In other words, the listed steps or options need not be exhaustive.

Unless indicated otherwise, all percentages for amount or amounts of ingredients used are to be understood to be percentages by weight based on the active weight of the material in the total weight of the composition, which total is 100%.

The invention relates to a process of enhancing conversion of taurine to alkyl taurate amide using specifically phosphoric acid as catalyst.

Specifically, it relates to process in which taurine or taurine salt is reacted with $C_8$ to $C_{22}$, preferably $C_8$ to $C_{20}$ fatty acid at defined ratios of fatty acid to the taurine or taurine salts. Use of the phosphoric acid is found to provide enhanced yield and/or efficiency and, further, there is no observable browning.

As indicated, the invention relates to a reaction in which a fatty acid is reacted (e.g., $C_8$ to $C_{22}$ or $C_8$ to $C_{20}$, fatty acid, preferably straight chain and saturated; preferably $C_{10}$ to $C_{18}$ fatty acid, again preferably straight chain and saturated; more preferably $C_{10}$ to $C_{14}$ fatty acid). More specifically, fatty acid is reacted with a taurine and/or taurine salt at defined molar ratios of fatty acid to the taurine and/or taurine salt. If more than one fatty acid is used, the ratio is defined as the molar ratio of all fatty acid in the mixture to taurine or taurine salt. The reaction takes place in the presence of specific phosphoric acid catalyst and is run within reaction temperature and a defined reaction time ranges noted.

As indicated use of $C_{10}$ to $C_{14}$, particularly $C_{12}$ fatty acid is highly preferred when using range of $C_8$ to $C_{22}$, or $C_8$ to $C_{20}$ fatty acid. For example, 50 to 100% is preferably $C_{10}$ to $C_{14}$ and preferably $C_{12}$ fatty acid. In a preferred embodiment, 100% of the fatty acid may be $C_{12}$, i.e., $C_{12}$ is the sole reacting fatty acid.

The fatty acid reacts with taurine or taurine salt, e.g., $NH_2CH_2CH_2SO_3^-M^+$, where $M^+$ may be sodium or potassium counterion.

The invention comprises a process for reaction of fatty acid or mixture of fatty acid (a preferred fatty acid is $C_{12}$ straight chain fatty acid) with taurine and/or taurine salt wherein
  a) the molar ratio of fatty acid to taurine (or salt) is 1.5:1 to 10:1, preferably 1.6:1 to 7:1, or 1.7:1 to 5:1;
  b) reaction temperature is 180° C. to 250° C., preferably 190 to 245° C., even more preferably 200 to 245° C.; and
  c) time of reaction is 1 to 10, preferably 1 to 6 hours.

As indicated above, the fatty acid reacts with taurine or taurine salt, e.g., $NH_2CH_2CH_2SO_3^-M^+$ where $M^+$ may be a sodium or potassium counterion.

As noted, the molar ratio of fatty acid or of total fatty acids to taurine or taurine salt is 1.5:1 to 10:1, preferably 1.6:1 to 7:1.

The reaction temperature is 180° C. to 250° C., preferably 190 to 245° C., more preferably 200 to 245° C. In some aspects, temperature of reaction is 220° C. to 245° C. and catalyst is used at 0.1 to 0.7, preferably 0.3 to 0.6%.

The reaction time is 1 to 100, preferably 1 to 6 hours, more preferably 2 to 5 hours.

While various catalysts have been used in the noted reaction for production of alkyl taurate amide, applicants are unaware of the disclosure of using specifically phosphoric acid, let alone the enhanced yields found relative to use of other catalysts.

Catalyst is present at level of 0.1% to 0.7 by wt., preferably 0.1% to 0.5% by wt.

The invention further relates to alkyl taurate amides made by the process of claim 1.

Process

Typical process is set forth below.
1. In a four necks 250 ml round bottom flask, equipped with mechanical stirrer, condenser, solvent trap/receiver and thermocouple/nitrogen ($N_2$) flow inlet, sodium N-methyl taurine (92.78 g, 61.53% solution, 1 eq.) was added. The $N_2$ flow was set to 0.2 liter per minute (LPM).
2. The reaction temperature was increased to about 240° C., and lauric acid (141.91 g, 2 eq.) and phosphoric acid (1.18 g, 85% solution) were added. Phosphoric acid was added in an amount of 0.5 wt. %. The reaction mixture was stirred at 240° C. for one to four hours.

EXAMPLES

TABLE 1

Examples 1-5 and Comparatives A-F

| Example | Catalyst | Amt. of catalyst (%) | Temp | Time | Yield |
|---|---|---|---|---|---|
| Comp. A | $H_3PO_2$ | 0.5 | 240° C. | 1 hr | 91.3 |
| Comp. B | $NaPO_2H_2$ | 0.5 | 240° C. | 1 hr | 88.1 |
| Example 1 | $H_3PO_4$ | 0.5 | 240° C. | 1 hr | 93.8 |
| Example 2 | $H_3PO_4$ | 0.5 | 240° C. | 1 hr | 92.8 |
| Comp. C | $H_3PO_2$ | 0.5 | 240° C. | 2 hr | 91.5 |
| Comp. D | $NaPO_2H_2$ | 0.5 | 240° C. | 2 hr | 91.7 |
| Example 3 | $H_3PO_4$ | 0.5 | 240° C. | 2 hr | 97.9 |
| Example 4 | $H_3PO_4$ | 0.5 | 240° C. | 2 hr | 98.8 |
| Comp. E | $H_3PO_2$ | 0.5 | 240° C. | 3 hr | 91.2 |
| Comp. F | $NaPO_2H_2$ | 0.5 | 240° C. | 3 hr | 92.1 |
| Example 5 | $H_3PO_4$ | 0.5 | 240° C. | 3 hr | 98.4 |

TABLE 2

Examples 6-8 and Comparatives G-L

| Example | Catalyst | Amt. of catalyst (%) | Temp | Time | Yield |
|---|---|---|---|---|---|
| Comp. G | $H_3PO_2$ | 0.3 | 240° C. | 1 hr | 89.8 |
| Comp. H | $NaPO_2H_2$ | 0.3 | 240° C. | 1 hr | 86.8 |
| Example 6 | $H_3PO_4$ | 0.3 | 240° C. | 1 hr | 92.6 |
| Comp. I | $H_3PO_2$ | 0.3 | 240° C. | 2 hr | 90.7 |
| Comp. J | $NaPO_2H_2$ | 0.3 | 240° C. | 2 hr | 89.3 |
| Example 7 | $H_3PO_4$ | 0.3 | 240° C. | 2 hr | 93.7 |
| Comp. K | $H_3PO_2$ | 0.3 | 240° C. | 3 hr | 91.2 |
| Comp. L | $NaPO_2H_2$ | 0.3 | 240° C. | 3 hr | 89.9 |
| Example 8 | $H_3PO_4$ | 0.3 | 240° C. | 3 hr | 96.5 |

From Tables 1 and 2, various things can be noted relating to unexpected beneficial effects of phosphoric acid ($H_3PO_4$) relative to other catalysts such as hypophosphorous ($H_3PO_2$) and sodium hypophosphite ($NaPO_2H_2$) used under exact same conditions.

Thus, in Examples 1 and 2 versus Comparative Examples A and B, it can be seen that, at identical amounts of catalysts, temperature and reaction time, phosphoric acid clearly provides superior yield. Examples 3 and 4 versus Comparatives C and D show the same enhanced benefit (e.g., 98.8% or 97.9% yield versus 91.7% or 91.5% yield for Comparatives) at a 2 hour reaction time. Again, Example 5 versus Comparatives E and F show same superior result for phosphoric acid versus other catalyst at a 3 hour reaction time.

Table 2 shows exactly the same results as Table 1 Example using 0.3% catalyst instead of 0.5% catalyst. In Example 6 versus Comparatives G and H, for example (0.3% catalyst, 240° C. temperature of reaction and 1 hour reaction time), phosphoric acid is superior. Same reaction at 2 hours and 3 hours (Example 7 versus Comparatives I and J; Example 8 versus Comparatives K and L) shows the same superiority of phosphoric acid in yield.

The products produced using phosphoric acid where white.

These results, based entirely on use of a particular catalyst versus other related catalysts, is completely unexpected.

TABLE 3

Examples 9-10 and Comparatives M, N, O and P

| Example | Catalyst | Amt. of catalyst (%) | Temperature | Time | Yield |
|---|---|---|---|---|---|
| Comp. M | ZnO | 0.5 | 195° C. | 1 hr. | 42.2 |
| Comp. N | $H_3PO_2$ | 0.5 | 195° C. | 1 hr. | 48.1 |
| Example 9 | $H_3PO_4$ | 0.5 | 195° C. | 1 hr. | 55.2 |
| Comp. O | ZnO | 0.5 | 195° C. | 2 hr. | 49.2 |
| Comp. P | $H_3PO_2$ | 0.5 | 195° C. | 2 hr. | 64.1 |
| Example 10 | $H_3PO_4$ | 0.5 | 195° C. | 2 hr. | 66.9 |

Examples 9 and 10 and Comparatives M to P (Table 3 above) demonstrate once more that, all other variables being equal, phosphoric acid provides surprising yield. In Table 3, run at lower temperatures than examples of Tables 1 and 2 (run at 195° C. versus 240° C.), yields are lower overall; however, phosphoric acid, relative to other catalysts (hypophosphorus, zinc oxide), provides superior yield even at these lower temperatures. One set of three examples was run for one hour and another set of three for two hours. All examples in Table 3 used 0.5% catalyst. As noted, this table demonstrates superiority not over just other phosphorus family catalysts, but also over zinc oxide, a well known and commonly used catalyst. The products produced using phosphoric acid where white.

TABLE 4

Examples 11 - and Comparatives Q, R, S and T

| Example | Catalyst | Amt. of catalyst (%) | Temperature | Time | Yield |
|---|---|---|---|---|---|
| Comp. Q | $H_3PO_2$ | 0.3 | 195° C. | 1 hr. | 43.3 |
| Example 11 | $H_3PO_4$ | 0.3 | 195° C. | 1 hr. | 51.4 |
| Comp. R | $H_3PO_2$ | 0.3 | 195° C. | 2 hr. | 64.6 |
| Example 12 | $H_3PO_4$ | 0.3 | 195° C. | 2 hr. | 67.9 |
| Comp. S | $H_3PO_2$ | 0.3 | 195° C. | 3 hr. | 77.2 |
| Example 13 | $H_3PO_4$ | 0.3 | 195° C. | 3 hr. | 80.3 |
| Comp. T | $H_3PO_2$ | 0.3 | 195° C. | 4 hr. | 86.7 |
| Example 14 | $H_3PO_4$ | 0.3 | 195° C. | 4 hr. | 87.8 |

Table 4 shows the same pattern of relative superiority of phosphoric acid compared to other catalysts (e.g., hypophosphorus). Again, using now 0.3% catalyst and reaction temperature of 195° C., pairs of reactions (phosphoric acid versus hypophosphorus in this table) were compared at 1, 2, 3 and 4 hour reaction, and yields using phosphoric acid as catalysts were superior in every case. The products produced using phosphoric acid where white.

The invention claimed is:

1. A process for making an N-alkyl taurate amide comprising reacting a $C_8$ to $C_{20}$ fatty acid with an alkali metal salt of an N-alkyl taurine, wherein:
    a) the molar ratio of the fatty acid to alkali metal salt is 1.5:1 to 10:1;
    b) a reaction temperature is from 180° C. to 250° C.;
    c) a catalyst is used in an amount of 0.1 to 0.7 wt %, based on the active weight of the catalyst in the total weight of the reaction mixture;
    d) a reaction time is 1 to 10 hours; and
    e) the catalyst is phosphoric acid.

2. The process according to claim 1, wherein reduced browning occurs relative to the use of hypophosphorous acid or zinc oxide catalysts in the same process.

3. The process according to claim 1, wherein the molar ratio of the fatty acid to alkali metal salt is 1.6:1 to 7:1.

4. The process according to claim 1, wherein the reaction temperature is 190 to 245° C.

5. The process according to claim 1, wherein the catalyst is used in an amount of 0.1 to 0.5 wt %, based on the active weight of the catalyst in the total weight of the reaction mixture.

6. The process according to claim 1, wherein the reaction time is 1 to 6 hours.

7. The process according to claim 1, wherein the N-alkyl taurate amide is white.

* * * * *